United States Patent
Stapert et al.

(10) Patent No.: US 11,604,249 B2
(45) Date of Patent: *Mar. 14, 2023

(54) INTERVENTIONAL DEVICE RECOGNITION

(71) Applicant: KONINKLIJKE PHILIPS N. V., Eindhoven (NL)

(72) Inventors: Hendrik Roelof Stapert, Rosmalen (NL); Carina Snuder, Eindhoven (NL); Ameet Kumar Jain, Boston, MA (US); Willem-Jan Arend De Wijs, Oss (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/673,955

(22) Filed: Feb. 17, 2022

(65) Prior Publication Data
US 2022/0196789 A1 Jun. 23, 2022

Related U.S. Application Data

(63) Continuation of application No. 15/778,715, filed as application No. PCT/EP2016/079522 on Dec. 2, 2016, now Pat. No. 11,275,150.

(Continued)

(30) Foreign Application Priority Data

Feb. 10, 2016 (EP) .................................. 16154967

(51) Int. Cl.
*G01S 5/30* (2006.01)
*A61B 8/08* (2006.01)
(Continued)

(52) U.S. Cl.
CPC .............. *G01S 5/30* (2013.01); *A61B 8/0841* (2013.01); *A61B 8/12* (2013.01); *A61B 8/4438* (2013.01);
(Continued)

(58) Field of Classification Search
None
See application file for complete search history.

(56) References Cited

U.S. PATENT DOCUMENTS

| 4,249,539 A | 2/1981 | Mezrich |
| 2010/0298704 A1 | 11/2010 | Pelissier |

(Continued)

FOREIGN PATENT DOCUMENTS

| WO | 2011138698 A1 | 11/2011 |
| WO | 2015101949 A1 | 7/2015 |

*Primary Examiner* — Katherine L Fernandez

(57) ABSTRACT

The present invention relates to an apparatus for tracking a position of an interventional device respective an image plane of an ultrasound field. The position includes an out-of-plane distance (Dop). A geometry-providing unit (GPU) includes a plurality of transducer-to-distal-end lengths ($Ltde_{1...n}$), each length corresponding to a predetermined distance (Ltde) between a distal end of an interventional device and an ultrasound detector attached to the interventional device, for each of a plurality of interventional device types ($T_{1...n}$). An image fusion unit (IFU) receives data indicative of the type (T) of the interventional device being tracked; and based on the type (T): selects from the geometry-providing unit (GPU), a corresponding transducer-to-distal-end length (Ltde); and indicates in a reconstructed ultrasound image (RUI) both the out-of-plane distance (Dop) and the transducer-to-distal-end length (Ltde) for the interventional device within the ultrasound field.

18 Claims, 3 Drawing Sheets

Related U.S. Application Data

(60) Provisional application No. 62/267,948, filed on Dec. 16, 2015.

(51) Int. Cl.
    *G01S 15/89*     (2006.01)
    *A61B 34/20*     (2016.01)
    *A61B 90/00*     (2016.01)
    *A61B 8/12*     (2006.01)
    *G01S 7/52*     (2006.01)
    *A61B 8/00*     (2006.01)
    *A61B 17/34*     (2006.01)
    *A61B 90/96*     (2016.01)
    *A61B 90/98*     (2016.01)

(52) U.S. Cl.
CPC ........ *A61B 8/4488* (2013.01); *A61B 17/3403* (2013.01); *A61B 34/20* (2016.02); *A61B 90/37* (2016.02); *G01S 7/52026* (2013.01); *G01S 7/52073* (2013.01); *G01S 15/899* (2013.01); *G01S 15/8915* (2013.01); *G01S 15/8918* (2013.01); *G01S 15/8977* (2013.01); *A61B 8/463* (2013.01); *A61B 90/96* (2016.02); *A61B 90/98* (2016.02); *A61B 2017/3413* (2013.01); *A61B 2034/2063* (2016.02); *A61B 2090/378* (2016.02); *A61B 2090/3782* (2016.02); *A61B 2090/3786* (2016.02)

(56) References Cited

U.S. PATENT DOCUMENTS

| | | |
|---|---|---|
| 2011/0245659 A1 | 10/2011 | Ma |
| 2011/0282188 A1 | 11/2011 | Burnside |
| 2015/0173723 A1 | 6/2015 | Bates |
| 2016/0324501 A1 | 11/2016 | Vignon |
| 2016/0367322 A1 | 12/2016 | Jain |
| 2017/0224426 A1 | 8/2017 | Lavallee |

| T | Ltde |
|---|---|
| $T_1$ | 5.0 mm |
| $T_2$ | 3.5 mm |
| $T_3$ | 10.1 mm |
FIG. 2
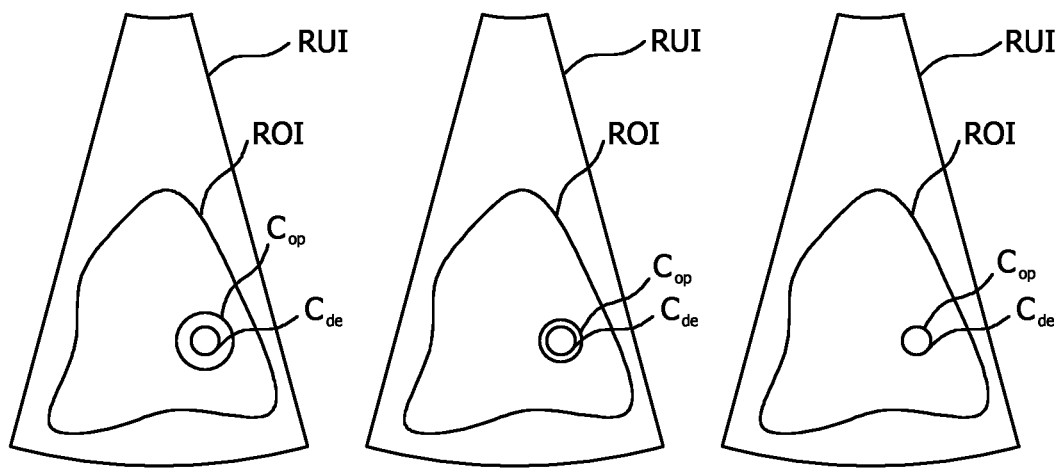
FIG. 3A  FIG. 3B  FIG. 3C
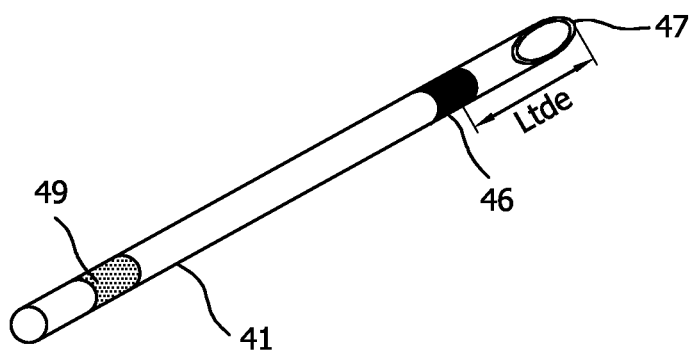
FIG. 4

INTERVENTIONAL DEVICE RECOGNITION

CROSS-REFERENCE TO PRIOR APPLICATIONS

This application is a Continuation of U.S. application Ser. No. 15/778,715, filed May 24, 2018, which is the U.S. National Phase application under 35 U.S.C. § 371 of International Application Serial No. PCT/EP2016/079522, filed on Dec. 2, 2016, which claims the benefit of U.S. Patent Application No. 62/267,948, filed on Dec. 16, 2015 and European Patent Application No. 16154967.0, filed on Feb. 10, 2016. This application is hereby incorporated by reference herein.

FIELD OF THE INVENTION

The present invention relates to the localization of an interventional device using ultrasound. More specifically it relates to the recognition of the type of interventional device that is attached to an ultrasound-based localization system.

BACKGROUND OF THE INVENTION

Interventional devices such as needles, catheters and surgical tools are often difficult to visualize in an ultrasound image due to the specular nature of their reflectivity, particularly at unfavorable incidence angles.

In one solution to this problem, U.S. Pat. No. 4,249,539 describes an arrangement in which the tip of a medical needle includes an ultrasound transducer that is responsive to the ultrasound signals emitted by an ultrasound imaging system. Upon detecting an ultrasound pulse from the ultrasound imaging system, a circuit connected to the transducer triggers the insertion of the needle position into the ultrasound image through either the generation of a return ultrasound pulse from the needle tip, or through the simulation of such a return pulse using a time of flight delay.

In another solution to this problem, patent application WO2011138698 describes a system for tracking an instrument in an ultrasound field with an ultrasound receiver that is mounted to the instrument. The 3D position of the ultrasound receiver is obtained by beamforming the signals received by it as the ultrasound beams of the ultrasound field sweep its field of view. The position of the ultrasound receiver is then displayed in the ultrasound image.

Document WO2015101949A1 discloses a tool navigation system employing an ultrasound probe, an ultrasound scanner, an interventional tool, a plurality of ultrasound transducers, a tool tracker and an image navigator. During an ultrasound scan, the interventional tool is navigated within the anatomical region relative to the acoustic image plane, and the ultrasound transducers facilitate tracking by the tool tracker of a position of the interventional tool relative to the acoustic image plane. One or more aspects of a graphical icon are modulated by the image navigator responsive to the tracked distance of the interventional tool relative to the acoustic image plane.

Document US20110282188A1 discloses a needle guidance system that utilizes ultrasound imaging. In one embodiment, the guidance system comprises an imaging device including a probe for producing an image of an internal body portion target. One or more sensors on the probe sense the magnetic field of a magnet included with the needle. The system includes a display for depicting the position and/or orientation of the needle together with the image of the target.

Document WO2014207666A1 discloses a system for tracking an instrument with ultrasound. The system includes a probe for transmitting and receiving ultrasonic energy and a transducer associated with the probe and configured to move with the probe during use. A medical instrument includes a sensor configured to respond to the ultrasonic energy received from the probe. A control module is stored in memory and configured to interpret the ultrasonic energy received from the probe and the sensor to determine a three dimensional location of the medical instrument and to inject a signal to the probe from the transducer to highlight a position of the sensor in an image.

Document US20100298704A1 discloses an ultrasound system that has an ultrasound transducer equipped with a position marker and a needle equipped with a position marker. The position markers allow the position and orientation of the transducer and needle to be determined. A display depicts an ultrasound image acquired via the transducer and a graphical element representative of a projection of the longitudinal axis of the needle onto a plane of the ultrasound image.

A drawback of the above-mentioned systems arises from the fact that it is the position of the ultrasound detector that is determined and subsequently displayed in the ultrasound image. Typically a user is interested in the position of a particular functional part of the instrument, such as the distal end of a needle, rather than the positon of the ultrasound detector itself. However, the mechanical constraints of such instruments hampers the ability to position the ultrasound detector at-will, for example at the tip of a needle where it might interfere with insertion. Another drawback of known localization systems occurs more specifically when they are used in conjunction with a planar ultrasound imaging system. Owing to the separation between the ultrasound detector being tracked and the functional part on the instrument, the ultrasound detector may be out-of-plane when the functional part is in-plane, but poorly visible under ultrasound. Thus it would be beneficial to indicate when a functional part of the instrument, such as the tip of a needle, is in-plane.

SUMMARY OF THE INVENTION

In seeking to alleviate the drawbacks of known localization systems, an apparatus is provided for determining a position of an interventional device respective an image plane of an ultrasound field defined by a plurality of beams emitted by an ultrasound transducer array of a beamforming ultrasound imaging system in which the position is determined based on ultrasound signals emitted by the ultrasound transducer array that have been detected by an ultrasound detector attached to the interventional device. The apparatus includes an image reconstruction unit, a position determination unit, a geometry-providing unit and an image fusion unit. The image reconstruction unit is configured to provide a reconstructed ultrasound image corresponding to the image plane based on the ultrasound signals detected by the ultrasound transducer array. The position determination unit is configured to identify, based on a correlation of the ultrasound signals emitted by the ultrasound transducer array with the ultrasound signals detected by the ultrasound detector, the position of the interventional device respective the image plane. Moreover the position of the interventional device includes an out-of-plane distance corresponding to the shortest distance between the ultrasound detector and the image plane. The geometry-providing unit comprises a plurality of transducer-to-distal-end lengths, wherein each length corresponds to a predetermined distance between a distal end of an interventional device and an ultrasound detector attached to the interventional device, for each of a plurality of interventional device types. The image fusion unit is configured to i) receive data indicative of the type of the interventional within the ultrasound field; and based on the type of the interventional device to ii) select from the geometry-providing unit, a corresponding transducer-to-distal-end length; and to iii) indicate in the reconstructed ultrasound image both the out-of-plane distance and the transducer-to-distal-end length for the interventional device within the ultrasound field.

In so doing, an apparatus is provided which can be used to track the position of an interventional device within an ultrasound field. Depending on the particular type of interventional device that is being tracked, the geometry-providing unit selects the corresponding transducer-to-distal-end length, and indicates this in the reconstructed image in combination with the out-of-plane distance of the ultrasound transducer. Thus, the apparatus provides improved determination of the position of the distal end of the interventional device. Moreover, because both the transducer-to-distal-end length and the out-of-plane distance are indicated in the reconstructed image, the position of the distal end of the interventional device in relation to the image plane is more accurately determined.

In accordance with another aspect of the invention the image fusion unit is further configured to i) indicate the out-of-plane distance in the reconstructed ultrasound image as the radius of a first circle; and to ii) indicate the transducer-to-tip length in the reconstructed ultrasound image as the radius of a second circle. The first circle and the second circle share a common centre, and the common centre corresponds to the position of the ultrasound detector. In so doing the determination of the position of the distal end of the interventional device respective the image plane of the beamforming ultrasound imaging system is improved because the first circle and the second circle coincide when the tip of the interventional device is in-plane.

In accordance with another aspect of the invention an interventional device that is adapted for use with the apparatus is described. The interventional device includes an ultrasound detector and a data carrier. The ultrasound detector is adapted for detecting ultrasound signals emitted by an ultrasound transducer array of a beamforming ultrasound imaging system. Moreover the ultrasound detector is attached to the interventional device at a predetermined distance from a distal end of the interventional device. The data carrier comprises data indicative of a type of the interventional device. Moreover, when this data, is received by the image fusion unit of the apparatus, the image fusion unit is caused to: i) select from the geometry-providing unit of the apparatus, a transducer-to-distal-end length corresponding to the predetermined distance between the distal end of the interventional device and the ultrasound detector attached thereto, for the interventional device type; and ii) to indicate in the reconstructed ultrasound image that is reconstructed by the image reconstruction unit of the apparatus of claim 1 the transducer-to-distal-end length for the interventional device within the ultrasound field.

In so doing the data stored in the data carrier of the interventional device, when received by the apparatus, brings about the benefit of improved determination of the position of the distal end of the interventional device respective the image plane of the beamforming ultrasound imaging system.

In accordance with another aspect of the invention a computer program product is disclosed. The computer program product may be used in conjunction with the apparatus.

It is to be noted that the various aspects or embodiments described in relation to the apparatus may also be used in combination or isolation with aspects or embodiments of the interventional device, and likewise with aspects and embodiments of the computer program product, and vice versa.

BRIEF DESCRIPTION OF THE FIGURES

FIG. 2 illustrates an exemplary lookup table 23 that includes a plurality of transducer-to-distal-end lengths Ltde for each of a plurality of corresponding interventional device types T.

FIGS. 3A, 3B, and 3C illustrate examples of a reconstructed ultrasound image RUI that include a region of interest ROI and in which both the out-of-plane distance Dop and the transducer-to-distal-end length Ltde are illustrated as circles Cop and Cde respectively.

FIG. 4 illustrates an intervention device 41 that is suitable for use with the first embodiment of the invention.

DETAILED DESCRIPTION OF THE INVENTION

In order to illustrate the principles of the present invention, various systems are described in which the position of an interventional device, exemplified by a medical needle, is determined within the image plane of an ultrasound field defined by the beams emitted by the linear array of a 2D ultrasound imaging probe.

It is however to be appreciated that the invention also finds application in determining the positon of other interventional devices such as a catheter, a guidewire, a probe, an endoscope, an electrode, a robot, a filter device, a balloon device, a stent, a mitral clip, a left atrial appendage closure device, an aortic valve, a pacemaker, an intravenous line, a drainage line, a surgical tool such as a tissue sealing device or a tissue cutting device.

It is also to be appreciated that the invention finds application in beamforming ultrasound imaging systems having other types of imaging probes and other types of ultrasound arrays which are arranged to provide a planar image, such as the 2D array of a 3D imaging probe, a "TRUS" transrectal ultrasonography probe, an "IVUS" intravascular ultrasound probe, a "TEE" transesophageal probe, a "TTE" transthoracic probe, a "TNE" transnasal probe, an "ICE" intracardiac probe.

Figure 1:
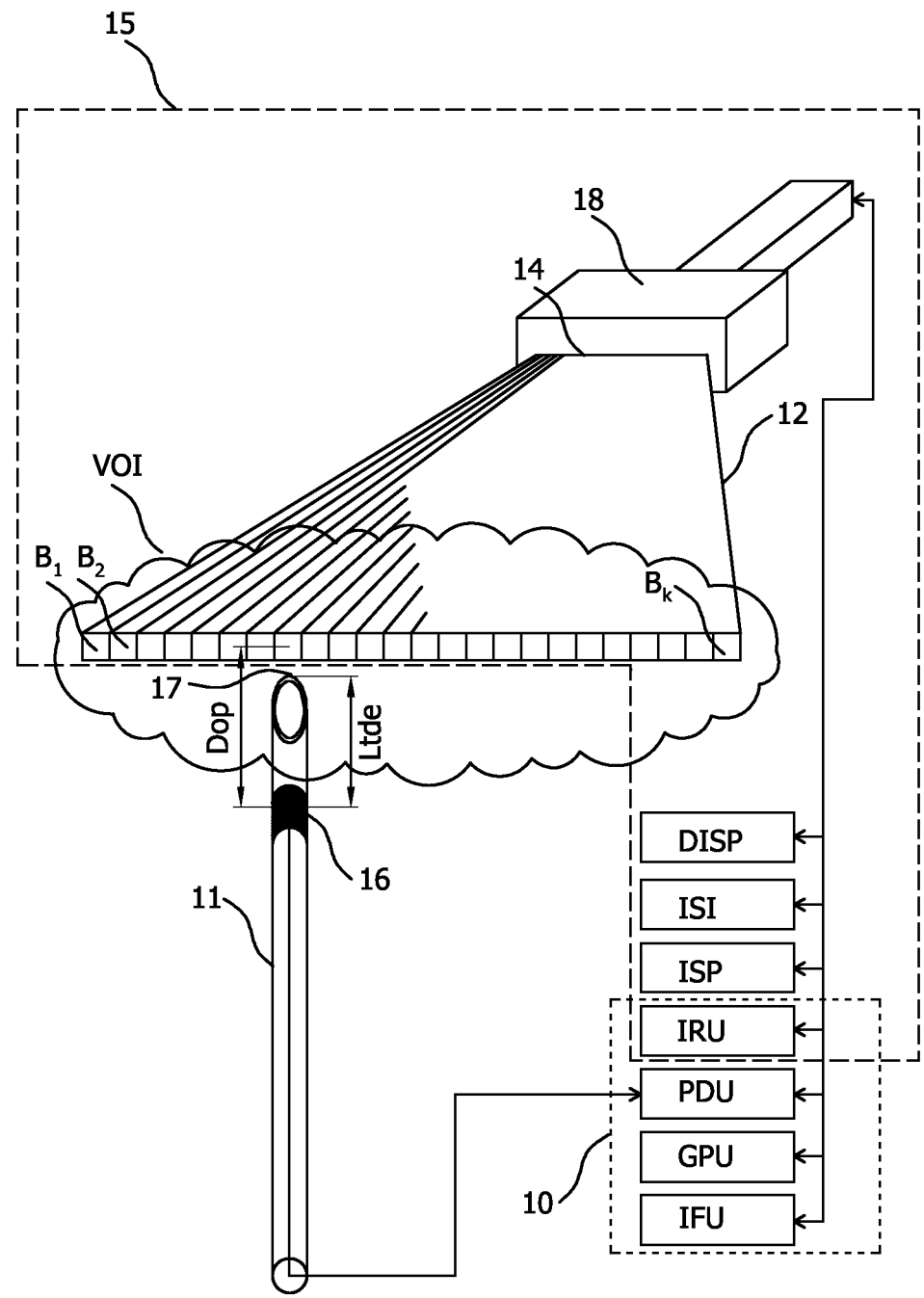
FIG. 1 illustrates a beamforming ultrasound imaging system 15 in combination with an interventional device 11 and a first embodiment of the invention 10.

FIG. 1 illustrates a beamforming ultrasound imaging system 15 in combination with an interventional device 11 and a first embodiment of the invention 10. In FIG. 1, beamforming ultrasound imaging system 15 includes a 2D ultrasound imaging probe 18 which is in communication with image reconstruction unit IRU, imaging system processor ISP, imaging system interface ISI and display DISP. The units IRU, ISP, ISI and DISP are conventionally located in a console with which 2D ultrasound imaging probe 18 is in wired communication. It is also contemplated that wireless communication, for example using an optical, infrared, or an RF communication link, may replace the wired link. It is also contemplated that some of units IRU, ISP, ISI and DISP may alternatively be located within 2D ultrasound imaging probe 76, as is the case for example in the Philips VISIQ ultrasound imaging system. In FIG. 1, 2D imaging probe 18 includes linear ultrasound transducer array 14 that transmits and receives ultrasound energy within an ultrasound field that intercepts volume of interest VOL. The ultrasound field is fan-shaped in FIG. 1 and includes multiple ultrasound beams $B_{1...k}$ that define an image plane 12. Beamforming ultrasound imaging system 15 may also include electronic driver and receiver circuitry (not shown) that is configured to amplify and/or to adjust the phase of signals transmitted by or received by 2D ultrasound imaging probe 18 in order to generate and detect the ultrasound signals in beams $B_{1...k}$. The electronic driver and receiver circuitry may thus be used to steer the emitted and/or received ultrasound beam direction.

In-use, the beamforming ultrasound imaging system 15 is operated in the following way. An operator may plan an ultrasound procedure via imaging system interface ISI. Once an operating procedure is selected, imaging system interface ISI triggers imaging system processor ISP to execute application-specific programs that generate and interpret the signals transmitted to and detected by 2D ultrasound imaging probe 18. Beamforming ultrasound imaging system 15 may also include a memory (not shown) for storing such programs. The memory may for example store ultrasound beam control software that is configured to control the sequence of ultrasound signals transmitted by and/or received by imaging probe 18. Image reconstruction unit IRU, which may alternatively form part of imaging system processor ISP, reconstructs data received from the imaging probe 18 into an image corresponding to image plane 12 and which thus intercepts volume of interest VOI, and subsequently displays this image via display DISP. The reconstructed image may for example be an ultrasound Brightness-mode "B-mode" image, otherwise known as a "2D mode" image, a "C-mode" image or a Doppler mode image, or indeed any ultrasound planar image.

Also shown in FIG. 1 is an interventional device 11 and a first embodiment of the invention 10 that may be used to track the position of interventional device 11 respective image plane 12 of beamforming ultrasound imaging system 15. The first embodiment of the invention 10 includes image reconstruction unit IRU, position determination unit PDU, geometry providing unit GPU, and image fusion unit IFU, each of these units being in communication with one another as illustrated by the interconnecting arrows. Interventional device 11 that is to be tracked, includes an ultrasound detector 16 that is positioned at a predetermined distance Ltde from distal end 17 of interventional device 11.

In-use, the position of interventional device 11, or more specifically that of ultrasound detector 16 attached thereto, is tracked respective image plane 12 by position determination unit PDU based on the ultrasound signals corresponding to its beams $B_{1...k}$ that have been detected by ultrasound transducer 16. Position determination unit PDU identifies the position of ultrasound detector 16 based on a correlation of the ultrasound signals emitted by the ultrasound transducer array with the ultrasound signals detected by the ultrasound detector. More specifically this correlation may be based on i) the time delay between emission of each beam $B_{1...k}$ and its detection by ultrasound detector 16, and ii) based on the amplitude of the ultrasound signals corresponding to each beam detected by the ultrasound detector. In more detail, the correlation essentially determines the ultrasound detector 16 position that, based on the emitted sequence of ultrasound signals, most closely matches the detected ultrasound signals. This may be illustrated as follows. When the ultrasound detector 16 is in the vicinity of image plane 12, ultrasound signals from the nearest of beams $B_{1...k}$ to the detector will be detected with a large amplitude whereas more distant beams will be detected with relatively smaller amplitudes. This amplitude can be modeled to vary in dependence on the range between the emitter and the detector, and the out-of-plane distance Dop between the detector 16 and the image plane 12. Moreover the time delay between emission and detection of the beam depends upon the range between the emitter and the detector for each emitted beam. The range is determined by multiplying the time delay by the speed of ultrasound propagation. The correlation between the ultrasound signals emitted by the ultrasound transducer array with the ultrasound signals detected by the ultrasound detector determines the best fit position of ultrasound detector 16 respective image plane 12. The out-of-plane distance may also be obtained by triangulating the position of the detector respective the ultrasound image plane.

The geometry-providing unit GPU of the first embodiment includes a plurality of transducer-to-distal-end lengths. Moreover, each length corresponds to a predetermined distance between a distal end of an interventional device and an ultrasound detector attached to the interventional device, for each of a plurality of interventional device types. The geometry-providing unit GPU may, for example, be provided by a lookup table. FIG. 2 illustrates an exemplary lookup table 23 that includes a plurality of transducer-to-distal-end lengths Ltde for each of a plurality of corresponding interventional device types T. Lookup table 23 in FIG. 2 may be used in the geometry-providing unit GPU of FIG. 1. In FIG. 1, type $T_1$ may for example correspond to a vascular access needle having an ultrasound transducer positioned 5.0 mm from its distal end, type $T_2$ may for example be a catheter, and exemplary interventional device type $T_3$ may be a tissue sealing tool. Other types of interventional device may be included in the lookup table in the same way.

The image fusion unit IFU of the first embodiment is arranged to receive data indicative of the type T of the interventional device within the ultrasound field. Moreover, based on the type T of the interventional device, the image fusion unit IFU selects from the above-described geometry-providing unit GPU, a corresponding transducer-to-distal-end length Ltde; and indicates in the reconstructed ultrasound image that is reconstructed by the image reconstruction unit IRU, both the out-of-plane distance Dop and the transducer-to-distal-end length Ltde for the interventional device within the ultrasound field. Since both the out-of-plane distance Dop and the transducer-to-distal-end length Ltde are indicated in the reconstructed image by image fusion unit IFU, it is immediately apparent when the distal end of the interventional device is in image plane 12. Moreover, the image fusion unit IFU that automatically selects the corresponding transducer-to-distal-end length Ltde from the geometry-providing unit GPU allows the tracking system to operate with different types of interventional device, and to correctly indicate their geometry in the reconstructed ultrasound image.

Each of the units: image fusion unit IFU, geometry-providing unit GPU, position determination unit PDU, and image reconstruction unit IRU may be provided by one or more processors including instructions to perform its respective function. Moreover, one or more of these units may be provided by imaging system processor ISP of beamforming ultrasound imaging system 15.

In one implementation the type T of the interventional device may be received by image fusion unit IFU wirelessly from a data carrier associated with the interventional device. In this example the data carrier may be, for example, an RFID chip, or a barcode or a QR code. In another example the data may be received via wired communication with the data carrier, for example from a memory associated with the interventional device. Thus the data carrier may be, for example, an RFID chip, or a barcode such as a linear or matrix barcode or a QR code, a memory or indeed any machine-readable data carrier. The image fusion unit may thus include a reader such as a barcode reader, an RFID reader, or a data reader for reading a memory, for reading the data in the data carrier. Alternatively a user may input this data manually to the image fusion unit.

The out-of-plane distance Dop and the transducer-to-distal-end length Ldte may be indicated in the reconstructed ultrasound image by various means, including in the form of a numerical indicator, a dial, or as a shape having a size that corresponds to the respective distance, or length. This may be provided for example as an overlay image on the reconstructed image, i.e. by fusing data from the indicator with the ultrasound image. Various colors may also be used to provide the desired indication. In preferred examples that are illustrated in FIGS. 3A, 3B, and 3C, circles are used as the indicators. FIGS. 3A, 3B, and 3C illustrate examples of a reconstructed ultrasound image RUI that include a region of interest ROI and in which both the out-of-plane distance Dop and the transducer-to-distal-end length Ltde are illustrated as circles Cop and Cde respectively. In this example, the image fusion unit IFU is arranged to indicate the out-of-plane distance in the reconstructed ultrasound image as the radius of a first circle Cop; and to indicate the transducer-to-tip length in the reconstructed ultrasound image as the radius of a second circle Cde. Moreover the first circle and the second circle share a common centre, and the common centre corresponds to the position of the ultrasound detector. In FIG. 3A the tip of the interventional device is somewhat out-of-plane, and Dop>Ltde, as indicated by the radius of circle of Cop exceeding that of Cde. As the tip of the interventional device is advanced towards the image plane the difference between the radii of the circles Cop and Cde decreases, as illustrated in FIG. 3B. When the tip of the interventional device is in-plane the radii of the circles Cop and Cde are the same and the perimeters of the circles coincide, as illustrated in FIG. 3C. In this way, a user is assisted in determining the position of the tip of the interventional device respective the ultrasound image plane. As to the actual position of the tip of the interventional device on the image plane, the common centre of the two circles is located at the closest point to the position of the ultrasound detector. However the exact position of the tip of the interventional device depends on the angle of a line between the interventional device tip and the ultrasound detector, respective the image plane. In conventional use of the interventional device with the beamforming ultrasound imaging system, this line is typically close to perpendicular to the image plane and thus the tip will lie at the common centre of the circles. Confirmation of this perpendicular arrangement is provided to a user during insertion of the interventional device in the region of interest ROI because in this arrangement the common centre remains in a fixed position respective on the image plane during insertion. As this line deviates from a perpendicular position the position of the tip in the ultrasound image is moved away from the common centre, but is always within the circle Cde. When the interventional device is inserted into a region of interest, intermittent images of the tip of the interventional device as provided by the beamforming ultrasound imaging system, and the displacement of parts of the region of interest, also confirm the indications provided by the circles.

Optionally, the image fusion unit may be further configured such that when the perimeter of the first circle and the perimeter of the second circle coincide, the first circle and the second circle are indicated as a common circle and at least one of the following occurs i) the perimeter of the common circle is indicated in a color that differs from the color of the first circle and from the color of the second circle; ii) the perimeter of the common circle is indicated with a contrast that differs from the contrast of the first circle and from the contrast of the second circle; iii) the common circle is displayed with a dashed perimeter; iv) the perimeter of the common circle is configured to pulse over time. These indications in the common circle alert to a user that the tip of the interventional device is in-plane respective the image plane of the ultrasound imaging system.

FIG. 4 illustrates an intervention device 41 that is suitable for use with the first embodiment of the invention. The interventional device includes an ultrasound detector 46 and a data carrier 49. The ultrasound detector is adapted for detecting ultrasound signals emitted by an ultrasound transducer array of a beamforming ultrasound imaging system. Ultrasound detector 46 is attached to interventional device 41 at a predetermined distance Ltde from a distal end 47 of interventional device 41. Data carrier 49 includes data indicative of a type T of interventional device 41. Moreover, this data, when received by the image fusion unit IFU of the first embodiment of the invention, causes image fusion unit IFU to i) select from the geometry-providing unit GPU of the first embodiment of the invention, a transducer-to-distal-end length Ltde corresponding to the predetermined distance between the distal end 47 of the interventional device 41 and the ultrasound detector 46 attached thereto, for the interventional device type T; and to ii) indicate in the reconstructed ultrasound image RUI that is reconstructed by the image reconstruction unit IRU of the first embodiment of the invention the transducer-to-distal-end length Ltde for the interventional device within the ultrasound field.

In FIG. 4, data carrier 49 may for example be a barcode such as a linear or matrix barcode or a QR code, an RFID chip, a memory, or indeed any machine-readable data carrier. The data carrier may be attached to the interventional device by various known means including adhesives, or it may be applied by printing, etching, and the like. Also, whilst illustrated as being disposed on the interventional device 41, data carrier 49 may alternatively be positioned on the packaging of interventional device 41, for example for sterility reasons.

Thus, when the interventional device of FIG. 4 is used with the first embodiment of the invention, i.e. item 10 in FIG. 1, the data received by the image fusion unit IFU enables the technical effect of improved determination of the position of the interventional device respective the image plane of the beamforming ultrasound imaging system.

Optionally the data carrier's data, when received by the image fusion unit IFU of FIG. 1 further causes the image fusion unit to indicate the transducer-to-tip length in the reconstructed ultrasound image as the radius of a second circle; i.e. Cde in FIGS. 3A, 3B, and 3C.

Optionally the data carrier's data, when received by the image fusion unit IFU of FIG. 1 further causes the image fusion unit to indicate in the reconstructed ultrasound image, an out-of-plane distance Dop corresponding to the shortest distance between the ultrasound detector and the image plane, as determined by the position determination unit PDU of the first embodiment of the invention.

Optionally the data carrier's data, when received by the image fusion unit IFU of FIG. 1 further causes the image fusion unit to indicate the out-of-plane distance Dop in the reconstructed ultrasound image RUI as the radius of a first circle Cop; wherein the first circle Cop and the second circle Cde share a common centre, and wherein the common centre corresponds to the position of the ultrasound detector.

Advantageously these additional effects that are triggered in the image fusion unit IFU bring about improved accuracy of determination of the position of the interventional device respective the image plane of the beamforming ultrasound imaging system.

Whilst the exemplary interventional device illustrated in FIG. 1 and FIG. 4 is a needle, other types of interventional device may be tracked in the same way with the above-described ultrasound detector, such as a catheter, a guidewire, a probe, an endoscope, an electrode, a robot, a filter device, a balloon device, a stent, a mitral clip, a left atrial appendage closure device, an aortic valve, a pacemaker, an intravenous line, a drainage line, a surgical tool such as a tissue sealing device or a tissue cutting device.

The ultrasound detector 46 illustrated in FIG. 1 and FIG. 4 may be provided by a number of piezoelectric materials, both hard and soft piezoelectric materials being suitable. Preferably ultrasound detector 46 is formed from Polyvinylidene fluoride, otherwise known as PVDF whose mechanical properties and manufacturing processes lend themselves to attachment to curved surfaces such as needles. Alternative materials include a PVDF co-polymer such as polyvinylidene fluoride trifluoroethylene, a PVDF ter-polymer such as P(VDF-TrFE-CTFE). Preferably the ultrasound detector is wrapped around an axis of the interventional device in order to provide sensing around 360 degrees of rotation about the axis although this need not always be the case. Moreover, the ultrasound detector may include various wires or a wireless communication module that are not shown in FIG. 4 for communicating detected ultrasound signals with the position determination unit PDU in FIG. 1. Preferably there is a single, i.e. one and only one, such ultrasound detector disposed on the interventional device. Advantageously this simplifies the form factor of the interventional device, any electrical interconnect that may be present, and the processing of any detected ultrasound signals. Alternatively, two or more ultrasound detectors may be used to provide position redundancy, and/or an indication of the trajectory of the interventional device.

Figure 5:
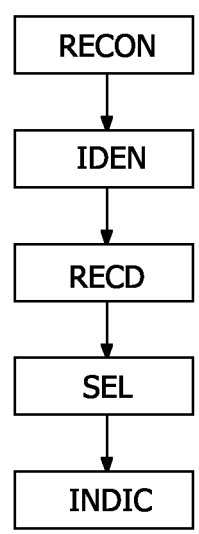
FIG. 5 illustrates various method steps, or instructions that may be carried out in accordance with apparatus 10 of FIG. 1.

FIG. 5 illustrates various method steps, or instructions that may be carried out in accordance with apparatus 10 of FIG. 1. The instructions may be stored on a computer program product and may be executed by or more processors. The method steps include: i) reconstructing, RECON, an ultrasound image corresponding to the image plane based on the ultrasound signals detected by the ultrasound transducer array; ii) identifying, IDEN, based on a correlation of the ultrasound signals emitted by the ultrasound transducer array with the ultrasound signals detected by the ultrasound detector, and optionally based on the time delay between emission of each beam and its detection by the ultrasound detector, and optionally based on the amplitude of the ultrasound signals corresponding to each beam detected by the ultrasound detector, the position of the interventional device respective the image plane; and wherein the position of the interventional device includes an out-of-plane distance corresponding to the shortest distance between the ultrasound detector and the image plane; iii) receiving data, RECD, indicative of a type of the interventional device within the ultrasound field; and based on the type of the interventional device: iv) selecting, SEL, from a lookup table, a transducer-to-distal-end length that corresponds to a predetermined distance between a distal end of the interventional device and the ultrasound detector attached to the interventional device; and v) indicating, INDIC, in the reconstructed ultrasound image, both the out-of-plane distance and the transducer-to-distal-end length for the interventional device within the ultrasound field. The instructions may also include one or more additional steps described herein in relation to FIG. 1.

The computer program product may be provided by dedicated hardware, or hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD.

In the above first, preferred embodiment described above in relation to FIG. 1-4 the data carrier of the interventional device includes data indicative of the needle type. In a second embodiment the data carrier may additionally or alternatively include data indicative of the transducer-to-distal-end length Ltde corresponding to the predetermined distance between the distal end of the interventional device and the ultrasound detector attached thereto. In this second embodiment the geometry-providing unit may thus be omitted from FIG. 1. Moreover the image fusion unit IFU of FIG. 1 may instead be configured to receive data indicative of the transducer-to-distal-end length Ltde of the interventional device; and to indicate in the reconstructed ultrasound image both the out-of-plane distance Dop and the transducer-to-distal-end length Ltde. In other words, in this embodiment, the type of the needle may no longer be used in the lookup process and the data carrier stores the distance between the distal end of the interventional device and the ultrasound detector attached thereto.

In a third embodiment of the invention, which may be used in combination with either the first or the second embodiments, or as an alternative thereto, the data carrier may include a data field indicative of one or more of the following: a length of the ultrasound detector along an axis extending between the ultrasound transducer and the distal end of the interventional device; a width of the ultrasound detector perpendicular to an axis extending between the ultrasound transducer and the distal end of the interventional device. Such data may also be indicated in the reconstructed image by the image fusion unit IFU. The respective parameter may for example be indicated in the form of the thickness of the perimeter of the first circle Cop or of the second circle Cde, or by third circle having a radius that corresponds to the extent of the ultrasound transducer and which shares a common centre with the second circle Cde. In this way perimeter thickness, or the extent of the third circle is indicative of the uncertainty of the position of the interventional device arising from the ultrasound detector's finite length and width. Either of these data fields may be stored on the data carrier and thus received therefrom by the image fusion unit IFU, or associated with the interventional device Type and stored in a lookup table similar to that of FIG. 2 and thus received by the image fusion unit IFU from the geometry providing unit GPU.

The invention claimed is:

1. A system for determining a position of an interventional device, the system comprising:
an image reconstruction processor configured to provide a reconstructed ultrasound image corresponding to an image plane of an ultrasound field defined by ultrasound signals emitted by an ultrasound imaging system;
a position determination processor configured to identify a position of the interventional device respective the image plane based on a correlation of the emitted ultrasound signals with ultrasound signals detected by an ultrasound detector attached to the interventional device, wherein the position includes an out-of-plane distance corresponding to a distance between the ultrasound detector and the image plane; and
an image fusion processor configured to:
receive data indicative of a transducer-to-distal-end length of the interventional device, wherein the transducer-to-distal-end length corresponds to a predetermined distance between a distal end of the interventional device and the ultrasound detector, and
indicate in the reconstructed ultrasound image (i) the out-of-plane distance by a first shape having a first size and (ii) the transducer-to-distal-end length by a second shape having a second size.

2. The system of claim 1, wherein the image fusion processor is configured to receive the data indicative of the transducer-to-distal-end length from a data carrier associated with the interventional device.

3. The system of claim 2, wherein the data carrier is disposed on the interventional device.

4. The system of claim 2,
wherein the data carrier is one of an RFID chip, a linear barcode, a matrix barcode, a QR code, or memory associated with the interventional device; and
wherein the image fusion processor includes one of a RFID reader, barcode reader, or other type of reader configured to read data in the data carrier.

5. The system of claim 1, further comprising:
a geometry-providing unit comprising a plurality of transducer-to-distal-end lengths, wherein each length corresponds to a predetermined distance between a distal end of a respective interventional device and a respective ultrasound detector attached to the respective interventional device, for each of a plurality of interventional device types; and
wherein the received data indicative of a transducer-to-distal-end length includes a type of the interventional device, and the image fusion processor is further configured to:
based on the type of the interventional device, select from the geometry-providing unit, the transducer-to-distal-end length.

6. The system of claim 1, wherein the first shape and the second shape share a common center, and the common center corresponds to a position of the ultrasound detector within the ultrasound field.

7. The system of claim 1,
wherein the first shape is a first circle and the first size is a radius of the first circle; and
wherein the second shape is a second circle and the second size is a radius of the second circle.

8. The system of claim 7, wherein the image fusion processor is further configured, when a perimeter of the first circle and a perimeter of the second circle coincide as a common circle, to indicate the first circle and the second circle as at least one of:
a perimeter of the common circle is indicated in a color that differs from a color of the first circle and from a color of the second circle;
the perimeter of the common circle is indicated with a contrast that differs from a contrast of the first circle and from a contrast of the second circle;
the common circle is displayed with a dashed perimeter; and
the perimeter of the common circle is configured to pulse over time.

9. The system of claim 1, wherein the ultrasound imaging system comprises an imaging probe that is one of: a 2D ultrasound imaging probe, a 3D ultrasound imaging probe, a transrectal ultrasonography probe, an intravascular ultrasound probe, a transesophageal probe, a transthoracic probe, a transnasal probe, or an intracardiac probe.

10. The system of claim 1, wherein the ultrasound detector is formed from a piezoelectric material that is one of a Polyvinylidene fluoride, a PVDF co-polymer, or a PVDF ter-polymer.

11. The system of claim 1, wherein the ultrasound field is defined by a plurality of beams ($B_{1 \ldots k}$) emitted by an ultrasound transducer array of the ultrasound imaging system and the ultrasound signals that provide the reconstructed ultrasound image are detected by the ultrasound transducer array.

12. The system of claim 1, wherein the interventional device is one of: a needle, a catheter, a guidewire, a probe, an endoscope, an electrode, a robot, a filter device, a balloon device, a stent, a mitral clip, a left atrial appendage closure device, an aortic valve, a pacemaker, an intravenous line, a drainage line, a surgical tool, or a tissue cutting device.

13. A method of determining a position of an interventional device, the method comprising:
reconstructing an ultrasound image corresponding to an image plane of an ultrasound field defined by ultrasound signals emitted by an ultrasound imaging system;
identifying a position of the interventional device respective the image plane based on a correlation of the emitted ultrasound signals with ultrasound signals detected by an ultrasound detector attached to the interventional device, wherein the position includes an out-of-plane distance corresponding to a distance between the ultrasound detector and the image plane;

receiving data indicative of a transducer-to-distal-end length of the interventional device, wherein the transducer-to-distal-end length corresponds to a predetermined distance between a distal end of the interventional device and the ultrasound detector; and indicating in the reconstructed ultrasound image (i) the out-of-plane distance by a first shape having a first size and (ii) the transducer-to-distal-end length by a second shape having a second size.

14. The method of claim 13, wherein the data indicative of the transducer-to-distal-end length is received from a data carrier associated with the interventional device, and wherein the data carrier is one of an RFID chip, a linear barcode, a matrix barcode, a QR code, or memory associated with the interventional device.

15. The method of claim 13, wherein the received data indicative of a transducer-to-distal-end length includes a type of the interventional device, and the method further comprises:

based on the type of the interventional device, selecting from a geometry-providing unit, the transducer-to-distal-end length, and wherein the geometry-providing unit comprises a plurality of transducer-to-distal-end lengths, wherein each length corresponds to a predetermined distance between a distal end of a respective interventional device and a respective ultrasound detector attached to the respective interventional device, for each of a plurality of interventional device types.

16. The method of claim 13, wherein the first shape and the second shape share a common center, and the common center corresponds to a position of the ultrasound detector within the ultrasound field.

17. The method of claim 13, wherein the first shape is a first circle and the first size is a radius of the first circle; and wherein the second shape is a second circle and the second size is a radius of the second circle.

18. The method of claim 17, further comprising: when a perimeter of the first circle and a perimeter of the second circle coincide as a common circle, indicating the first circle and the second circle as at least one of:

a perimeter of the common circle is indicated in a color that differs from a color of the first circle and from a color of the second circle;

the perimeter of the common circle is indicated with a contrast that differs from a contrast of the first circle and from a contrast of the second circle;

the common circle is displayed with a dashed perimeter; and the perimeter of the common circle is configured to pulse over time.

* * * * *